(12) United States Patent
Geissler et al.

(10) Patent No.: US 6,392,047 B1
(45) Date of Patent: May 21, 2002

(54) PROCESS FOR PREPARING BIARYLS IN THE PRESENCE OF PALLADOPHOSPHACYCLOBUTANE CATALYSTS

(75) Inventors: Holger Geissler, Mainz; Steffen Haber, Landau/Pfalz; Andreas Meudt, Floersheim-Weilbach; Frank Vollmueller, Mainz; Stefan Scherer, Buettelborn, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/615,486

(22) Filed: Jul. 13, 2000

(30) Foreign Application Priority Data

Jul. 13, 1999 (DE) .......................................... 199 32 571

(51) Int. Cl.⁷ ...................... C07D 401/04; C07D 307/40
(52) U.S. Cl. .................... 546/260; 549/484; 549/83; 548/564; 585/425; 585/467; 585/469; 546/259; 546/276.4; 546/280.4; 546/283.4

(58) Field of Search .................................. 546/259, 260, 546/276.4, 280.4, 283.4; 548/564; 549/83, 484; 585/425, 467, 469

(56) References Cited

U.S. PATENT DOCUMENTS 5,559,277 A * 9/1996 Beller et al. ................. 585/469
6,084,114 A    7/2000 Geissler et al.
6,194,627 B1 * 2/2001 Geissler et al. ............. 585/436

FOREIGN PATENT DOCUMENTS

DE            196 47 584          5/1998

* cited by examiner

Primary Examiner—Charanjit S. Aulakh
(74) Attorney, Agent, or Firm—Scott E. Hanf

(57) ABSTRACT

Biaryls, e,g,. biphenyls, phenylpyridines, phenylfurans, phenylpyrroles, phenylthiophenes, bipyridines, pyridylfurans or pyridylpyrroles are prepared in high yields by coupling aromatics with an aromatic boric acid or boric ester in the presence of a palladaphosphacyclobutane catalyst.

13 Claims, No Drawings

PROCESS FOR PREPARING BIARYLS IN THE PRESENCE OF PALLADOPHOSPHACYCLOBUTANE CATALYSTS

BACKGROUND OF THE INVENTION

The number of important intermediates in the chemical industry which contain a biaryl structure has increased greatly in recent years. Owing to their applications in the pharmaceutical and agricultural sectors, producers of such intermediates are concerned not only with price, but also with the high purity requirements. For these reasons, highly active, stable and highly selective catalyst systems for the C,C couplings mostly employed for preparing unsymmetrical biaryls are sought. Particularly in the case of couplings of nonactivated aromatics, especially chloroaromatics, the catalyst systems known hitherto generally require the use of large amounts of catalyst (up to 5 mol % or more) in order to achieve industrially useful conversions. Nevertheless, the compositions of the reaction mixtures obtained are often so complex that simple recycling of the catalyst is no longer possible and as a result the high catalysts costs stand in the way of industrial implementation.

SUMMARY OF THE INVENTION

It is therefore an object of the present invention to prepare biaryls in high yields, high selectivity and high purity and to use catalyst systems which can be obtained simply and inexpensively and are stable on storage, lead to a high TON (turnover number) and TOF (turnover frequency) and have long operating lives.

It has surprisingly been found that palladaphosphacyclobutanes meet the abovementioned requirements and even in very small amounts make Suzuki couplings, even of chloroaromatics, possible under gentle conditions. The reaction products are obtained in high yields and in high purity even after only simple and inexpensive purification steps. Astonishingly, the palladaphosphacyclobutanes used at the same time have very high activity and high stability so that it is possible to use very small amounts of catalyst. The small amounts of catalyst result in economic and ecological advantages since waste products and waste-intensive work-up processes are avoided. The process of the invention thus meets the demands which are made of a process which can readily be implemented in industry.

DESCRIPTION OF THE PREFERRED EMBODIMENTS

The present invention provides a process for preparing biaryls of the formula (1),

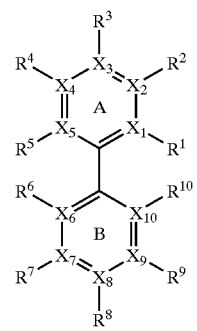

(I)

where $R^1$ to $R^{10}$ are identical or different and are each, independently of one another, hydrogen, straight-chain or branched alkyl having from 1 to 8 carbon atoms, cycloalkyl which has from 3 to 7 carbon atoms in the ring and may bear $C_1$–$C_4$-alkyl(s) as substituent(s), $C_2$–$C_8$-alkenyl, $C_2$–$C_8$-alkynyl, fluorine, chlorine, hydroxy, OLi, ONa, OK, $OMg_{0.5}$, OMgCl, OMgBr, alkoxy having from 1 to 8 carbon atoms, $NH_2$, NHR', $NR'_2$, NH(C=O)R', NH(C=O)OR', NH(C=O)$NR'_2$, $NO_2$, $SO_2R'$, SOR', $POphenyl_2$, PO—($C_1$–$C_8$-alkyl)$_2$, $PO_3$—($C_1$–$C_8$-alkyl)$_2$, (C=O)R', C(=O)$NR'_2$, C(=O)OR', CN, $CO_2Li$, $CO_2Na$, $CO_2K$, $CO_2MgCl$, $CO_2MgBr$, phenyl, substituted phenyl, aralkyl or heteroaryl; or two adjacent radicals $R^{(n)}$ and $R^{(n+1)}$ correspond to a bridging 1,ω-alkanediyl chain having from 3 to 8 carbon atoms or a bridging ethylene dioxy or methylene dioxy chain; or two adjacent radicals $R^{(n)}$ and $R^{(n+1)}$ correspond to a unit of the formula

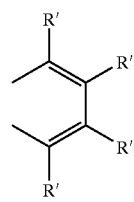

and the radicals R' are, independently of one another, hydrogen, $C_{1-C_8}$-alkyl, $C_1$–$C_8$-alkoxy or phenyl, and the ring atoms $X_1$ to $X_{10}$ are either all carbon atoms (biphenyls) or at most one heteroatom is present in each of the two linked rings A and B such that any ring member $R^iX_i$ is N (phenylpyridines, bipyridines), or two adjacent ring members $R^2X_2$ and $R^3X_3$, or $R^4X_4$ and $R^5X_5$, or $R^7X_7$ and $R^8X_8$, or $R^9X_9$ and $R^{10}X_{10}$, are replaced by S, O or NR" (e.g. phenylthiophenes, phenylpyrroles, phenylfurans, pyridylfurans, pyridylpyrroles), where R" is hydrogen, alkyl having from 1 to 8 carbon atoms, $SiR'_3$ or C(=O)R', by coupling aromatics of the formula (2) with an aromatic boron compound of the formula (3),

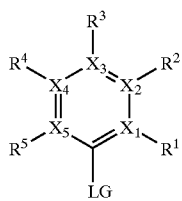

(2)

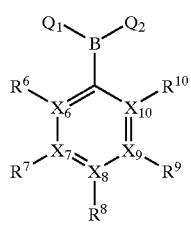

(3)

where LG is one of the leaving groups fluorine, chlorine, bromine, iodine, triflate, perfluoro-$(C_1-C_8)$alkylsulfonate, mesylate, tosylate, nosylate (p-nitrophenylsulfonate), brombenzenesulfonate or $N(OSO_2CF_3)_2$;

$Q_1$ and $Q_2$ are identical or different and are each OH or a radical of the formula —O—$(C_1-C_8)$alkyl, —O—$(C_2-C_8)$-alkenyl, —O—$(C_2-C_8)$alkynyl, —O-aryl or —O-alkylaryl, or $Q_1$, $Q_2$ and the adjacent boron atom form a cyclic boric ester of the alcohols $(C_3-C_{12})$-cycloalkane-1,2-diol, $(C_5-C_{12})$-cycloalkene-1,2-diol, $(C_5-C_{12})$-cycloalkane-1,3-diol, $(C_5-C_{12})$-cycloalkene-1,3-diol or of alcohols of the formulae (Va) to (Ve),

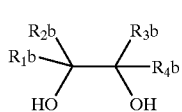

Va

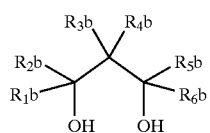

Vb

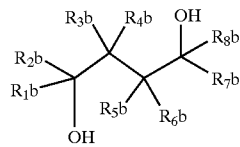

Vc

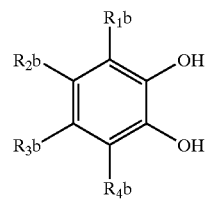

Vd

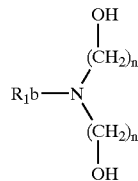

Ve where $R_1b$ to $R_8b$ are identical or different and are each, independently of one another, hydrogen, $C_1-C_{12}$-alkyl, $C_1-C_{12}$-hydroxyalkyl, $C_2-C_{12}$-alkenyl, $C_2-C_{12}$-alkynyl, $C_3-C_{12}$-cycloalkyl, $(C_1-C_{12})$-alkoxy, $(C_1-C_{12})$-acyloxy, O-phenyl, O-benzyl, aryl, heteroaryl, fluorine, chlorine, bromine, iodine, $NO_2$, $NH_2$, $N(alkyl)_2$, $N[Si(C_1-C_4-alkyl)_3]_2$, $CF_3$, $CCl_3$ or $CBr_3$, and/or two adjacent radicals $R_1b$ to $R_8b$ together form a 5- to 8-membered aliphatic or aromatic ring, e.g. a phenyl ring, and n is an integer from 2 to 12, or $Q_1$ and $Q_2$ together form a divalent radical of the formula (Vf)

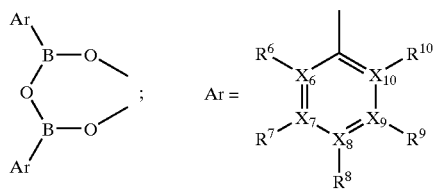

Vf wherein the coupling is carried out in the presence of a palladium compound of the formula (IV),

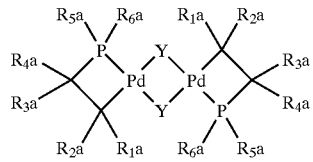

IV where $R_1a$ and $R_2a$ are each, independently of one another hydrogen, $(C_1-C_4)$-alkyl, $(C_3-C_{12})$-cycloalkyl, $(C_1-C_4)$-alkoxy, fluorine, $N(C_1-C_4-alkyl)_2$, $CO_2$—$(C_1-C_4$-alkyl), OCO—$(C_1-C_4)$-alkyl or substituted or unsubstituted aryl;

$R_3a$, $R_4a$, $R_5a$ and $R_6a$ are, independently of one another, $(C_1-C_8)$-alkyl, $(C_3-C_8)$-cycloalkyl, substituted or unsubstituted aryl;

or $R_1a$ and $R_2a$, or $R_2a$ and $R_3a$, or $R_3a$ and $R_4a$, together form an aliphatic ring having from 4 to 10 carbon atoms, or $R_5a$ and $R_6a$ together with the P atom form a saturated or unsaturated 4- to 9-membered ring, or $R_4a$ and $R_5a$ form a bridging 1,ω-alkanediyl chain having from 2 to 7 carbon atoms;

and

Y is an anion of an inorganic or organic acid, a α,γ-diketo compound or a 5- or 6-membered nitrogen-containing heterocycle, and in the presence of a base and a solvent at temperatures of from 20° C. to 200° C.

The process of the invention makes it possible to prepare, for example, biphenyls, phenylpyridines, phenylfurans, phenylpyrroles, phenylthiophenes, bipyridines, pyridylfurans and pyridylpyrroles.

Preference is given to compounds of the formula (1) in which $R^1$ to $R^{10}$ are identical or different and are each hydrogen, straight-chain or branched $C_1$–$C_4$-alkyl, $C_5$–$C_6$-cycloalkyl, methyl-($C_5$–$C_6$)cycloalkyl, $C_2$–$C_4$-alkenyl, $C_2$–$C_4$-alkynyl, fluorine, chlorine, hydroxy, $C_2$–$C_4$-alkoxy, $NH_2$, NHR', NR'$_2$, NHCOR', NHCOOR', COOH, COOR', CN, phenyl, a phenyl, benzyl or pyridyl substituted by from 1 to 3 radicals selected from the group consisting of $C_1$–$C_4$-alkyl, F, Cl, $C_2$–$C_4$-alkoxy or $NO_2$, or two adjacent radicals $R^{(n)}$ and $R^{(n+1)}$ form a 1,ω-alkyldiyl chain having from 4 to 6 carbon atoms, and R' is hydrogen, $C_1$–$C_4$-alkyl, $C_1$–$C_6$-alkoxy or phenyl.

Preferred aromatic boron compounds of the formula (3) are ones in which $R^6$ to $R^{10}$ are as defined above and $Q_1$ and $Q_2$ are each a radical of the formula OH, —O—($C_1$–$C_4$)-alkyl, —O—($C_2$–$C_4$)-alkenyl, —O—($C_2$–$C_4$)-alkynyl, O-phenyl or —O-benzyl, or $Q_1$, $Q_2$ and the adjacent boron atom form a cyclic boric ester of the alcohols ethylene glycol, 1,3-propanediol, 1,4-butanediol, 2,2-dimethylpropane-1,3-diol, catechol, pinacol, 2,3-dihydroxynaphthalene, diethanolamine, triethanolamine, 1,2-dihydroxycyclohexane, 1,3-dihydroxycyclopentane or 1,2-dihydroxycyclooctane.

The synthesis of the catalysts of the formula (IV) is described in DE-A1-19647584. The palladaphosphacyclobutanes used generally have a dimeric structure. However, in the case of certain compounds (e.g. Y=acetylacetone, hexafluoroacetylacetone), monomeric, oligomeric or even polymeric structures can be present.

Preference is given to compounds of the formula (IV) in which $R_1$a and $R_2$a are, independently of one another, hydrogen, methyl, ethyl, cyclopentyl, cyclohexyl, methoxy, ethoxy, fluorine, phenyl, tolyl or naphthyl;

$R_3$a and $R_4$a are, independently of one another, ($C_1$–$C_4$)-alkyl, ($C_5$–$C_6$)-cycloalkyl, substituted or unsubstituted $C_6$–$C_{10}$-aryl, or $R_3$a and $R_4$a together form an aliphatic ring having 5 or 6 carbon atoms;

$R_5$a and $R_6$a are, independently of one another, ($C_1$–$C_4$)-alkyl, ($C_5$–$C_6$)-cycloalkyl, phenyl, naphthyl, anthracenyl, which may be unsubstituted or substituted by from 1 to 3 $CF_3$—, ($C_1$–$C_4$)-alkyl- or ($C_1$–$C_4$)-alkoxy groups;

and Y is acetate, propionate, benzoate, chloride, bromide, iodide, fluoride, sulfate, hydrogensulfate, nitrate, phosphate, triflate, tetrafluoroborate, tosylate, mesylate, acetylacetonate, hexafluoroacetylacetonate or pyrazolyl.

Particular preference is given to compounds in which $R_1$a and $R_2$a are, independently of one another, hydrogen or methyl;

$R_3$a and $R_4$a are, independently of one another, methyl, ethyl or phenyl, $R_5$a and $R_6$a are, independently of one another, phenyl, naphthyl, o-trifluoromethylphenyl, o-trifluoromethyl-p-tolyl, o-trifluoromethyl-p-methoxyphenyl, o-methoxyphenyl, o,p-dimethoxyphenyl, anthracenyl, tert-butyl, n-butyl, isopropyl, isobutyl, cyclohexyl or 1-methylcyclohexyl.

Very particular preference is given to the following compounds of the formula (IV):

trans-di-μ-acetato-bis[2-[bis(1,1-dimethylethyl)phosphino]-2-methylpropyl-C,P]dipalladium(II), trans-di-μ-acetato-bis[2-[1,1-dimethylethyl)phenylphosphino]-2-methylpropyl-C,P]dipalladium(II), trans-di-μ-chloro-bis[2-[bis(1,1-dimethylethyl)phosphino]-2-methylpropyl-C,P]dipalladium(II), trans-di-μ-chloro-bis[2-[1,1-dimethylethyl)-phenylphosphino]-2-methylpropyl-C,P]dipalladium(II), trans-di-μ-bromo-bis[2-[bis(1,1-dimethylethyl)phosphino]-2-methylpropyl-C,P]dipalladium(II) and trans-di-μ-bromo-bis[2-[1,1-dimethylethyl)phenylphosphino]-2-methylpropyl-C,P]dipalladium(II).

During the catalysis cycle, the dimeric structure is broken up by means of bridge cleavage reactions with inorganic and organic nucleophiles so that the actual catalytically active species are likely to be the mononuclear complexes of the formula (VI) or (VII).

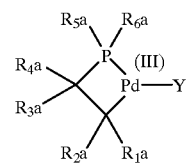

VI

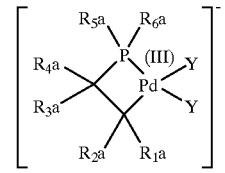

VII

The complexes of the formulae (VI) and (VII) are in equilibrium with the dimers actually used and are uncharged or anionic. The mononuclear complex of the formula (VI) may have further donor: ligands on the palladium atom.

The catalyst is advantageously used in a molar ratio to the compound of the formula (2) of from $10^{-6}$ to 1, preferably from $10^{-5}$ to 0.1, in particular from $10^{-5}$ to 0.01.

The stability of the palladophosphacyclobutanes in solution can be increased by addition of alkali metal salts, alkaline earth metal salts and transition metal salts of transition groups VI to VIII. In particular, the addition of halides and pseudohalides of the metals mentioned in many cases gives a significant increase in yield and improvement in the operating life of the catalyst. Other suitable salts are ammonium halides, trialkylammonium and tetraalkylammonium salts and also corresponding phosphonium and arsonium salts.

As ionic halide, preference is given to using ammonium bromide, lithium bromide, sodium bromide, potassium bromide, tetrabutylphosphonium bromide, ammonium chloride, tetramethylammonium chloride, diethanolammonium chloride, lithium chloride, sodium chloride, potassium chloride, tetrabutylphosphonium chloride, ammonium iodide, lithium iodide, sodium iodide, potassium iodide and/or tetrabutylphosphonium iodide. Particular preference is given to lithium chloride.

The abovementioned salts are advantageously added in amounts of from 0 to 250 mol %, for example from 10 to 100 mol %, based on the compound of the formula (3).

Solvents used are generally inert organic solvents. Examples of well suited solvents are aromatic hydrocarbons such as toluene, xylenes, anisole, tetralin and aliphatic ethers such as tetrahydrofuran, dimethoxyethane, dioxane, tetrahydropyran and formaldehyde acetals. The amount of solvent is advantageously from 1 to 5000% by weight, preferably from 25 to 2000% by weight, particularly preferably from 50 to 1500% by weight, based on the weight of the compound of the formula (3).

The coupling of the invention generally proceeds at temperatures of from 20 to 200°C.; in many cases it has been found to be useful to work at temperatures of from 50 to 165° C., preferably from 60 to 160° C.

Bases used are, in particular, alkali metal alkoxides or alkaline earth metal alkoxides, alkali metal amides or alkaline earth metal amides, alkali metal acetates or alkaline earth metal acetates, alkali metal formates or alkaline earth metal formates, alkali metal propionates or alkaline earth metal propionates, alkali metal or alkaline earth metal carbonates, hydrogencarbonates, hydroxides or oxides and also aliphatic or aromatic amines. Particularly preferred bases are sodium carbonate or potassium carbonate, sodium hydroxide or potassium hydroxide, sodium tert-butoxide or potassium tert-butoxide and pyridine. The base is preferably used in an amount of from 0.5 to 5 equivalents, preferably from 0.8 to 4 equivalents and particularly preferably from 1 to 2 equivalents, based on the boron compound of the formula (3) used.

The following examples illustrate the invention without restricting its scope.

SYNTHESIS OF THE CATALYST trans-Di-$\mu$-acetato-bis[2-[bis(1,1-dimethylethyl) phosphino]-2-methylpropyl-C,P]dipalladium A solution of 5.1 g of Pd(OAc)$_2$ (22.7 mmol) in 200 ml of toluene is admixed with 5.0 g (24.7 mmol) of tri(tert-butyl)phosphine. The color of the solution changes quickly from reddish brown to light orange. After heating at 70–80° C. for 10 minutes, cooling to room temperature and removal of the solvent under reduced pressure, 200 ml of hexane are added. The product which crystallizes after a short time is filtered off and washed with a little hexane. This gives 6.65 g (80%) of the whitish yellow catalyst. Recrystallization from hexane and filtration of the solutions through Celite enables the product to be obtained in analytically pure form as whitish yellow acicular crystals.

$^{31}$P-NMR (121.4 MHz, CDCl$_3$): –8.5 (s).

EXAMPLES

Example 1

Preparation of 4-Chlorobiphenyl

A mixture of 100 mmol of p-chlorophenylboronic acid (15.7 g), 98 mmol of bromobenzene (15.4 g), 110 mmol of anhydrous sodium carbonate (11.7 g), 0.1 mmol of trans-di-$\mu$-acetato-bis[2-[bis(1,1-dimethylethyl)phosphino]-2 methylpropyl-C,P]dipalladium (0.2 mol %), 10 mmol of lithium chloride (0.43 g) and 100 ml of tetrahydrofuran was refluxed for 2.5 hours. After distilling off as much of the THF as possible under atmospheric pressure and replacing it by 100 ml of toluene, the mixture was hydrolyzed with 150 ml of water. The aqueous phase was extracted with a further 50 ml of toluene and the organic phase was washed with 50 ml of water. Distillation of the combined organic phases gave 4-chlorobiphehyl in a yield of 97% (based on bromobenzene).

Example 2

Preparation of methyl 2-Phenylfuran-4-carboxylate 50 mmol of methyl 2-chlorofuran-4-carboxylate were heated with 52 mmol of phenylboronic acid, 50 mmol of potassium carbonate, 25 mmol of lithium chloride and 0.25 mmol of trans-di-$\mu$-acetato-bis[2-[bis(1,1-dimethylethyl) phosphino]-2-methylpropyl-C,P]dipalladium (1 mol %) in 150 ml of dibutylether at 80° C. for 8 hours. Aqueous work-up, filtration through a short silica gel column and distilling off the solvent leaves methyl 2-phenylfuran-4-carboxylate as a colorless residue. Yield: 85%.

Example 3

Preparation of 2,2'-Bipyridyl 50 mmol of 2-chloropyridine are refluxed together with 50 mmol of 2-pyridylboronic acid glycol ester, 25 mmol of lithium chloride, 50 mmol of potassium hydroxide, 1 mmol of tetrabutylammonium chloride and 0.05 mmol of trans-di-$\mu$-acetato-bis[2-[bis(1,1-dimethylethyl)phosphino]-2-methylpropyl-C,P]dipalladium (0.2 mol %) in (0.2 mol %) in 150 ml of tetrahydrofuran for 5 hours. Customary aqueous work-up and crystallization of the crude product from ethanol gives 2,2'-bipyridyl as colorless crystals (m.p. 70° C.) in a yield of 91%.

What is claimed is:
1. A process for preparing biaryls of the formula (1),

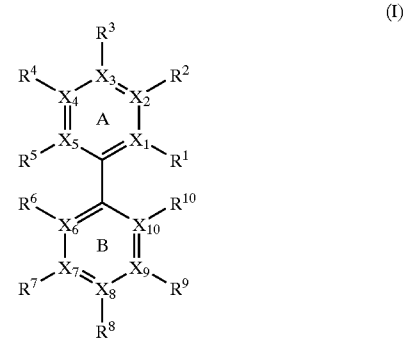

where
R$^1$ to R$^{10}$ are identical or different and are each, independently of one another, hydrogen, straight-chain or branched alkyl having from 1 to 8 carbon atoms, cycloalkyl which has from 3 to 7 carbon atoms in the ring and may bear C$_1$–C$_4$-alkyl(s) as substituent(s), C$_2$–C$_8$-alkenyl, C$_2$–C$_8$-alkynyl, fluorine, chlorine, hydroxy, OLi, ONa, OK, OMg$_{0.5}$, OMgCl, OMgBr, alkoxy having from 1 to 8 carbon atoms, NH$_2$, NHR', NR'$_2$, NH(C=O)R', NH(C=O)OR', NH(C=O)NR'$_2$, NO$_2$, SO$_2$R', SOR', POphenyl$_2$, PO—(C$_1$–C$_8$-alkyl)$_2$, PO$_3$—(C$_1$–C$_8$-alkyl)$_2$, C(=O)R', C(=O)NR'$_2$, C(=O) OR', CN, CO$_2$Li, CO$_2$Na, CO$_2$K, CO$_2$MgCl, CO$_2$MgBr, phenyl, substituted phenyl, aralkyl or heteroaryl; or two adjacent radicals R$^{(n)}$ and R$^{(n+1)}$ correspond to a bridging 1,ω-alkanediyl chain having from 3 to 8 carbon atoms or a bridging ethylene dioxy or methylene dioxy chain; or two adjacent radicals R$^{(n)}$ and R$^{(n+1)}$ correspond to a unit of the formula

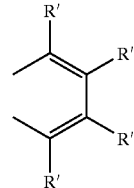

and the radicals R' are, independently of one another, hydrogen, C$_1$–C$_8$-alkyl, C$_1$–C$_8$-alkoxy or phenyl,
and the ring atoms X$_1$ to X$_{10}$ are either all carbon atoms or at most one heteroatom is present in each of the two linked rings A and B such that any ring member R$^i$X$_i$ is N, or two adjacent ring members R$^2$X$_2$ and R$^3$X$_3$, or R$^4$X$_4$ and R$^5$X$_5$, or R$^7$X$_7$ and R$^8$X$_8$, or R$^9$X$_9$ and R$^{10}$X$_{10}$, are replaced by S, O or NR", where R" is hydrogen, alkyl having from 1 to 8 carbon atoms, SiR'$_3$ or C(=O)R',
by coupling aromatics of the formula (2) with an aromatic boron compound of the formula (3),

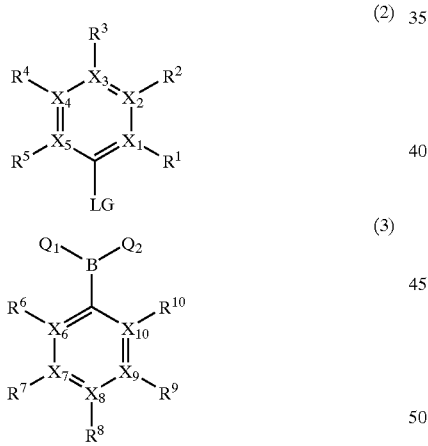

where LG is one of the leaving groups fluorine, chlorine, bromine, iodine, triflate, perfluoro-(C$_1$–C$_8$)alkylsulfonate, mesylate, tosylate, nosylate, brombenzenesulfonate or N(OSO$_2$CF$_3$)$_2$;

Q$_1$ and Q$_2$ are identical or different and are each OH or a radical of the formula —O—(C$_1$–C$_8$)alkyl, —O—(C$_2$–C$_8$)-alkenyl, —O—(C$_2$–C$_8$)alkynyl, —O-aryl or —O-alkylaryl, or Q$_1$, Q$_2$ and the adjacent boron atom form a cyclic boric ester of the alcohols (C$_3$–C$_{12}$)-cycloalkane-1,2-diol, (C$_5$–C$_{12}$)-cycloalkene-1,2-diol, (C$_5$–C$_{12}$)-cycloalkane-1,3-diol, (C$_5$–C$_{12}$)-cycloalkene-1,3-diol or of alcohols of the formulae (Va) to (Ve),

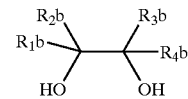
Va

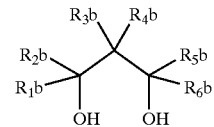
Vb

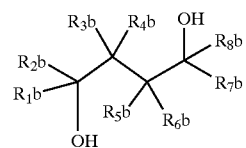
Vc

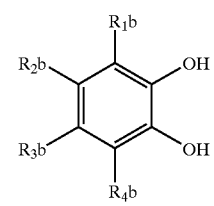
Vd

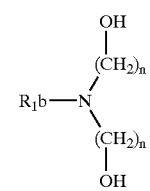
Ve where R$_1$b to R$_8$b are identical or different and are each, independently of one another, hydrogen, C$_1$–C$_{12}$-alkyl, C$_1$–C$_{12}$-hydroxyalkyl, C$_2$–C$_{12}$-alkenyl, C$_2$–C$_{12}$-alkynyl, C$_3$–C$_{12}$-cycloalkyl, (C$_1$–C$_{12}$-alkoxy, (C$_1$–C$_{12}$)-acyloxy, O-phenyl, O-benzyl, aryl, heteroaryl, fluorine, chlorine, bromine, iodine, NO$_2$, NH$_2$, N(alkyl)$_2$, N[Si (C$_1$–C$_4$-alkyl)$_3$]$_2$, CF$_3$, CCl$_3$ or CBr$_3$, and/or two adjacent radicals R$_1$b to R$_8$b together form a 5- to 8-membered aliphatic or aromatic ring, and n is an integer from 2 to 12, or Q$_1$ and Q$_2$ together form a divalent radical of the formula (Vf)

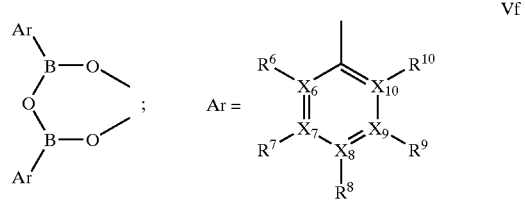
Vf wherein the coupling is carried out in the presence of a palladium compound of the formula (IV),

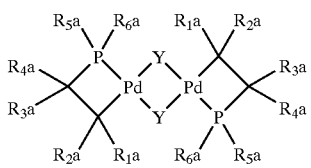

(IV)

where $R_1a$ and $R_2a$ are each, independently of one another hydrogen, $(C_1-C_4)$-alkyl, $(C_3-C_{12})$-cycloalkyl, $(C_1-C_4)$-alkoxy, fluorine, $N-(C_1-C_4$-alkyl$)_2$, $CO_2-(C_1-C_4$-alkyl), $OCO-(C_1-C_4)$-alkyl or substituted or unsubstituted aryl;

$R_3a$, $R_4a$, $R_5a$ and $R_6a$ are, independently of one another, $(C_1-C_8)$-alkyl, $(C_3-C_8)$-cycloalkyl, substituted or unsubstituted aryl;

or $R_1a$ and $R_2a$, or $R_2a$ and $R_3a$, or $R_3a$ and $R_4a$, together form an aliphatic ring having from 4 to 10 carbon atoms, or $R_5a$ and $R_6a$ together with the P atom form a saturated or unsaturated 4- to 9-membered ring, or $R_4a$ and $R_5a$ form a bridging 1,ω-alkanediyl chain having from 2 to 7 carbon atoms; and Y is an anion of an inorganic or organic acid, a α,γ-diketo compound or a 5- or 6-membered nitrogen-containing heterocycle, and in the presence of a base and a solvent at temperatures of from 20° C. to 200° C.

2. The process as claimed in claim 1, wherein the compound of the formula (1) is a biphenyl, phenylpyridine, phenylfuran, phenylpyrrole, phenylthiophene, bipyridine, pyridylfuran or pyridylpyrrole.

3. The process as claimed in claim 1, wherein $R^1$ to $R^{10}$ are identical or different and are each hydrogen, straight-chain or branched $C_1-C_4$-alkyl, $C_5-C_6$-cycloalkyl, methyl-$(C_5-C_6)$cycloalkyl, $C_2-C_4$-alkenyl, $C_2-C_4$-alkynyl, fluorine, chlorine, hydroxy, $C_2-C_4$-alkoxy, $NH_2$, NHR', $NR'_2$, NHCOR', NHCOOR', COOH, COOR', CN, phenyl, a phenyl, benzyl or pyridyl substituted by from 1 to 3 radicals selected from the group consisting of $C_1-C_4$-alkyl, F, Cl, $C_2-C_4$-alkoxy or $NO_2$ or two adjacent radicals $R^{(n)}$ and $R^{(n+1)}$ form a 1,ω-alkyldiyl chain having from 4 to 6 carbon atoms, and R' is hydrogen, $C_1-C_4$-alkyl, $C_1-C_6$-alkoxy or phenyl.

4. The process as claimed in claim 1, wherein $Q_1$ and $Q_2$ are each a radical of the formula OH, $-O-(C_1-C_4)$-alkyl, $-O-(C_2-C_4)$-alkenyl, $-O-(C_2-C_4)$-alkynyl, O-phenyl or O-benzyl; or $Q_1$ and $Q_2$ and the adjacent boron atom form a cyclic boric ester of the alcohols ethylene glycol, 1,3-propanediol, 1,4-butanediol, 2,2-dimethylpropane-1,3-diol, catechol, pinacol, 2,3-dihydroxynaphthalene, diethanolamine, triethanolamine, 1,2-dihydroxycyclohexane, 1,3-dihydroxycyclopentane or 1,2-dihydroxycyclooctane.

5. The process as claimed in claim 1, wherein $R_1a$ and $R_2a$ are each, independently of one another, hydrogen, methyl, ethyl, cyclopentyl, cyclohexyl, methoxy, ethoxy, fluorine, phenyl, tolyl or naphthyl;

$R_3a$ and $R_4a$ are each, independently of one another, $(C_1-C_4)$-alkyl, $(C_5-C_6)$-cycloalkyl, substituted or unsubstituted $C_6-C_{10}$-aryl, or $R_3a$ and $R_4a$ together form an aliphatic ring having 5 or 6 carbon atoms;

$R_5a$ and $R_6a$ are each, independently of one another, $(C_1-C_4)$-alkyl, $(C_5-C_6)$-cycloalkyl, phenyl, naphthyl, anthracenyl, which may be unsubstituted or substituted by from 1 to 3 $CF_3-$, $(C_1-C_4)$-alkyl or $(C_1-C_4)$-alkoxy groups;

and Y is acetate, propionate, benzoate, chloride, bromide, iodide, fluoride, sulfate, hydrogensulfate, nitrate, phosphate, triflate, tetrafluoroborate, tosylate, mesylate, acetylacetonate, hexafluoroacetylacetonate or pyrazolyl.

6. The process as claimed in claim 1, wherein $R_1a$ and $R_2a$ are, independently of one another, hydrogen or methyl; $R_3a$ and $R_4a$ are, independently of one another, methyl, ethyl or phenyl;

$R_5a$ and $R_6a$ are, independently of one another, phenyl, naphthyl, o-trifluoromethylphenyl, o-trifluoromethyl-p-tolyl, o-trifluoromethyl-p-methoxyphenyl, o-methoxyphenyl, o,p-dimethoxyphenyl, anthracenyl, tert-butyl, n-butyl, isopropyl, isobutyl, cyclohexyl or 1-methylcyclohexyl.

7. The process as claimed in claim 1, wherein the compound of the formula (IV) is trans-di-μ-acetato-bis[2-[bis(1,1-dimethylethyl)phosphino]-2-methylpropyl-C,P] dipalladium(II), trans-di-μ-acetato-bis[2-[1,1-dimethylethyl)phenylphosphino]2-methylpropyl-C,P] dipalladium(II), trans-di-μ-chloro-bis[2-[bis(1,1-dimethylethyl)phosphino]-2-methylpropyl-C,P]dipalladium (II), trans-di-μ-chloro-bis[2-[1,1-dimethylethyl)-phenylphosphino]-2-methylpropyl-C,P]dipalladium(II), trans-di-μ-bromo-bis-[2-[bis(1,1-dimethylethyl)phosphino]-2-methylpropyl-C,P]dipalladium(II) or trans-di-μ-bromo-bis[2-[1,1-dimethylethyl)phenylphosphino]-2-methylpropyl-C,P]dipalladium(II).

8. The process as claimed in claim 1, wherein the molar ratio of the palladium compound of the formula (IV) used to the compound of the formula (2) is from $10^{-6}$ to 1, preferably from $10^{-5}$ to 0.1.

9. The process as claimed in claim 1, wherein the coupling is carried out in the presence of a halide of an alkali metal or alkaline earth metal or transition metal of transition groups VI to VII or an ammonium, phosphonium or arsonium halide.

10. The process as claimed in claim 1, wherein the solvent used is an aromatic hydrocarbon or an aliphatic ether.

11. The process as claimed in claim 1, wherein the base used is an alkali metal alkoxide or alkaline earth metal alkoxide, alkali metal amide or alkaline earth metal amide, alkali metal acetate or alkaline earth metal acetate, alkali metal formate or alkaline earth metal formate, alkali metal propionate or alkaline earth metal propionate, alkali metal or alkaline earth metal carbonate, hydrogencarbonate, hydroxide or oxide or an aliphatic or aromatic amine.

12. The process as claimed in claim 1, wherein the coupling is carried out at a temperature of from 50 to 165° C.

13. The process as claimed in claim 12, wherein the coupling is carried out at a temperature of from 60 to 160° C.

\* \* \* \* \*